(12) United States Patent
Atanasoska et al.

(10) Patent No.: US 8,591,494 B2
(45) Date of Patent: Nov. 26, 2013

(54) ELECTROCHEMICAL THERAPEUTIC AGENT DELIVERY DEVICE

(75) Inventors: Liliana Atanasoska, Edina, MN (US); Rajesh Radhakrishnan, Maple Grove, MN (US); Robert W. Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 646 days.

(21) Appl. No.: 12/789,069

(22) Filed: May 27, 2010

(65) Prior Publication Data

US 2010/0318020 A1 Dec. 16, 2010

Related U.S. Application Data

(60) Provisional application No. 61/185,745, filed on Jun. 10, 2009.

(51) Int. Cl.
*A61M 31/00* (2006.01)
*A61M 29/00* (2006.01)
*A61N 1/30* (2006.01)

(52) U.S. Cl.
USPC .......... 604/509; 604/96.01; 604/21; 606/192; 606/194

(58) Field of Classification Search
USPC .......... 604/20–23, 501, 96.01, 103.01, 97.01, 604/509, 103.06, 264; 606/192, 194
See application file for complete search history.

(56) References Cited

U.S. PATENT DOCUMENTS

| | | | |
|---|---|---|---|
| 4,073,287 A * | 2/1978 | Bradley et al. | 600/373 |
| 5,354,264 A * | 10/1994 | Bae et al. | 604/21 |
| 5,628,730 A * | 5/1997 | Shapland et al. | 604/21 |
| 5,824,048 A | 10/1998 | Tuch | |
| 5,843,089 A | 12/1998 | Sahatjian et al. | |
| 6,064,908 A | 5/2000 | Muller et al. | |
| 6,123,718 A | 9/2000 | Tu et al. | |
| 6,537,195 B2 * | 3/2003 | Forman | 600/3 |
| 6,592,617 B2 | 7/2003 | Thompson | |
| 6,625,486 B2 | 9/2003 | Lundkvist et al. | |
| 6,899,731 B2 | 5/2005 | Li et al. | |
| 7,070,582 B2 | 7/2006 | Freyman et al. | |

(Continued)

FOREIGN PATENT DOCUMENTS

WO 93/07920 A1 4/1993

OTHER PUBLICATIONS

International Search Report and the Written Opinion of the International Searching Authority, mailed Jan. 13, 2011, from related international application No. PCT/US2010/036403.

(Continued)

*Primary Examiner* — Emily Schmidt
*Assistant Examiner* — Bradley G Thomas, Jr.
(74) *Attorney, Agent, or Firm* — Kenyon & Kenyon LLP (57) ABSTRACT

A therapeutic agent delivery device and method for eluting a therapeutic agent to a target location are disclosed. The device may comprise a first conductive element, a second conductive element, an electrochemical composition including an electrolyte and a therapeutic agent, and a permeable membrane covering the electrochemical composition. The first conductive element and the second conductive element are adapted to be connected to a voltage source. When the voltage source is connected to the first conductive element and the second conductive element, an electrochemical reaction occurs causing the therapeutic agent to pass through the permeable membrane and thereby to elute to a target location.

18 Claims, 3 Drawing Sheets

(56) References Cited

U.S. PATENT DOCUMENTS

| | | |
|---|---|---|
| 2006/0184092 A1* | 8/2006 | Atanasoska et al. ............ 604/20 |
| 2007/0208365 A1 | 9/2007 | Lee et al. |
| 2007/0208405 A1 | 9/2007 | Goodin et al. |
| 2007/0250036 A1 | 10/2007 | Volk et al. |
| 2008/0107794 A1 | 5/2008 | O'Connor et al. |

OTHER PUBLICATIONS

Morisato et al., Transport Properties of PA12-PTMO/AgBF4 Solid Polymer Electrolyte Membranes for Olefin/Paraffin Separation, Desalination 145 (2002), pp. 347-351, Elsevier Science B.V.

Furtado et al., Electrochemical Behavior of Polyurethane Ether Electrolytes/Carbon Black Composites and Application to Double Layer Capacitor, Electrochimica Acta 46 (2001), pp. 1629-1634, Elsevier Science Ltd.

Kujawski et al., Sweeping Gas Pervaporation with Hollow-Fiber Ion-Exchange Membranes, Desalination 162 (2004), pp. 129-135, Elsevier B.V.

Timbola et al., Electrochemical Oxidation of Quercetin in Hydro-Alcoholic Solution, J. Braz. Chem. Soc., vol. 17, No. 1 (2006), pp. 139-148, Sociedade Brasileira de Quimica.

Rezac et al., Effect of Copolymer Composition on the Solubility and Diffusivity fo Water and Methanol in a Series of Polyether Amides, J Appl. Polymer Sci. 65 (1997), pp. 1983-1993, John Wiley & Sons, Inc.

* cited by examiner

ELECTROCHEMICAL THERAPEUTIC AGENT DELIVERY DEVICE

CROSS REFERENCE TO RELATED APPLICATION

The present application claims priority to U.S. provisional application Ser. No. 61/185,745 filed Jun. 10, 2009, the disclosure of which is incorporated herein by reference in its entirety.

FIELD OF THE INVENTION

The present invention relates to the delivery of therapeutic agent, for example to the interior walls of a vessel such as a blood vessel, via a therapeutic agent delivery device.

BACKGROUND INFORMATION

Angioplasty and the delivery of therapeutic agent to the interior lumen walls are common medical practices in the treatment of stenosis and restenosis. Stenosis is a condition in which a region of a blood vessel has been narrowed to such a degree that blood flow is restricted. If the stenosis is severe, treatment is required to restore adequate blood flow. Despite treatment, in time, the site may undergo restenosis. Restenosis may occur because the treatment procedure sometimes creates cracks in plaque on the vessel wall which leave jagged surfaces that can induce blood clotting at the site. Another cause of restenosis is the development of intimal proliferation. This condition is characterized by excessive cell growth that is triggered by the trauma of the treatment.

Angioplasty involves the insertion of a catheter, e.g., a balloon catheter, into a blood vessel to expand an occluded region of the blood vessel, and is frequently used to treat arteriosclerosis. The balloon is inflated, often by injecting a suitable fluid into the balloon, at the site to widen the lumen and then deflated and removed from the body. Angioplasty has become a successful alternative to coronary arterial bypass surgery. The occluded area is compressed radially outward to increase the cross-sectional area of the artery so that the artery has an acceptable blood flow rate.

The delivery of therapeutic agent to the interior lumen walls of a diseased vessel can be useful in treating stenosis or restenosis. The delivery of the therapeutic agent can be completed through the use of numerous devices and/or procedures including direct injection by syringe and needle, pneumatic injection of the therapeutic agent into the diseased tissue, and the release of the therapeutic agent, near the target site, by the distal end of a catheter inserted into the lumen.

One method for delivery of therapeutic agent to the interior lumen walls is treatment of the balloon used in angioplasty procedures with therapeutic agent or therapeutic agent/polymer mixture such that when the balloon contacts the inner surface of the vascular lumen, the therapeutic agent is released into the adjacent tissue. Layered balloons with delivery ports for delivery of therapeutic agent through the ports to the inner surface of the lumen are known in the art, such as that disclosed in U.S. Pat. No. 5,843,089 to Sahatjian et al., which is expressly incorporated herein by reference.

Another method involves administering therapeutic agents systemically, e.g., orally or intravenously, to treat a restenosed site. In this case, a relatively large amount of the therapeutic agent must be administered so that, after being diluted during transport through the body, an effective dose reaches the site. Moreover, many parts of the body which are not diseased are still exposed to the therapeutic agent.

Another example of such procedures involves the use of stents. Stents are capable of maintaining intimate contact between a substance applied to the outer surface of the stent and the tissues of the vessel to be treated. Stents, however, can present challenges both with respect to securing a therapeutically significant amount of a substance on the stent during expansion of the stent into contact with the blood vessel wall, and also with respect to controlling the rate of drug delivery from the stent to the vessel wall.

U.S. Pat. No. 5,824,048 to Tuch describes an intravascular stent having a coating which includes a polymer and a therapeutic substance on the body of a stent, and in particular on its tissue-contacting surface, in which the coating has a greater concentration of therapeutic substance on the portion of the coating nearest the stent body than near the exterior surface of the coating. The inclusion of a polymer in intimate contact with a drug on the stent allows the drug to be retained on the stent in a resilient matrix during expansion of the stent and also slows the administration of the drug following implantation for improved application of therapeutic agent to the vessel.

U.S. Pat. No. 6,899,731 to Li et al., which is expressly incorporated herein by reference, discloses a method of delivering a negatively charged therapeutic agent to a target location within a mammalian body. The method comprises the steps of applying a multiplicity of alternating layers of at least one cationic polyelectrolyte carrier and a multiplicity of layers of a negatively charged therapeutic agent to at least one surface of an insertable medical device. The medical device is delivered to a target site within the body, and upon reaching the target site, the negatively charged therapeutic agent is released into the target site. The negatively charged therapeutic agent is disclosed as keeping therapeutic intact during the insertion and release stages.

Despite the advances in treatment of restenosis, it is desirable to provide better methods of delivery of therapeutic agent to a target location. Blood flow and particle interactions may diminish the volume and effectiveness of a therapeutic agent delivered to an occluded vessel through conventional procedures which employ stents, balloons, hydrogels and the like. Such inefficiencies lead to greater costs and more invasive procedures.

SUMMARY OF THE INVENTION

The invention is directed to improvements in devices for delivery of a therapeutic agent to a target location, such as the inside of a vessel.

In an embodiment of the invention, a therapeutic agent delivery device is provided comprising a first conductive element, a second conductive element, an electrochemical composition including an electrolyte and a therapeutic agent located between the first conductive element and the second conductive element, and a permeable membrane covering the electrochemical composition. The first conductive element and the second conductive element are adapted to be connected to a voltage source. In this embodiment, when the first conductive element and the second conductive element are connected to the voltage source, an electrochemical reaction occurs causing the therapeutic agent to pass through the permeable membrane and thereby to elute to a target location.

A disclosed further embodiment provides for a therapeutic agent delivery device in which the first conductive element is part of a first composite cable. In this embodiment, the first composite cable comprises the first conductive element, the electrochemical composition, and the permeable membrane. The permeable membrane surrounds the first conductive element, and the electrochemical composition is located between the first conductive element and the permeable membrane. When the first conductive element and the second conductive element are connected to the voltage source, the electrochemical reaction causes the therapeutic agent in the first composite cable to pass through the permeable membrane of the first composite cable to elute to a target location.

In a further embodiment, the second conductive element may be part of a second composite cable. The second composite cable comprises the second conductive element, a second electrochemical composition including an electrolyte and a therapeutic agent, and a second permeable membrane. The second permeable membrane surrounds the second conductive element, and the second electrochemical composition is located between the second conductive element and the second permeable membrane. When the first conductive element and the second conductive element are connected to the voltage source, an electrochemical reaction causes the therapeutic agent in the second composite cable to pass through the second permeable membrane of the second composite cable to elute to a target location.

A disclosed further embodiment provides for a therapeutic agent delivery device in which the first conductive element and the second conductive element are located on an expandable member and cross each other to form areas bounded by the first conductive element and the second conductive element. In a further embodiment, the electrochemical composition may be located in areas bounded by the first conductive element and the second conductive element, and the permeable membrane may be positioned to cover the areas bounded by the first conductive element and the second conductive element in which the electrochemical composition is located.

A disclosed further embodiment provides for a method of delivering a therapeutic agent to a target location The method comprises providing a therapeutic agent delivery device comprising a first conductive element adapted to be connected to a voltage source, a second conductive element adapted to be connected to the voltage source, an electrochemical composition located between the first conductive element and the second conductive element at a therapeutic agent delivery area of the device, the electrochemical composition including an electrolyte and a therapeutic agent, and a permeable membrane covering the electrochemical composition. In this embodiment, the method further comprises positioning the therapeutic agent delivery area of the device at a target location, and connecting the first conductive element and the second conductive element to the voltage source, thereby causing an electrochemical reaction that causes the therapeutic agent to pass through the permeable membrane and thereby to elute to the target location.

Depending on the embodiment, the invention can have advantages including reduced loss of therapeutic agent during and after the procedure, simplicity of design, reduced procedural complications, improved ease of use, and/or improved overall performance during and after the procedure. These and other features and advantages of the disclosed devices and methods are described in, or apparent from, the following detailed description of various exemplary embodiments.

BRIEF DESCRIPTION OF THE DRAWINGS

Various embodiments will be more readily understood through the following detailed description, with reference to the accompanying drawings, in which.

DETAILED DESCRIPTION

For a general understanding of the features of the illustrated embodiments of the invention, reference is made to the drawings. In the drawings, like reference numerals have been used throughout to designate like elements.

Figure 1:
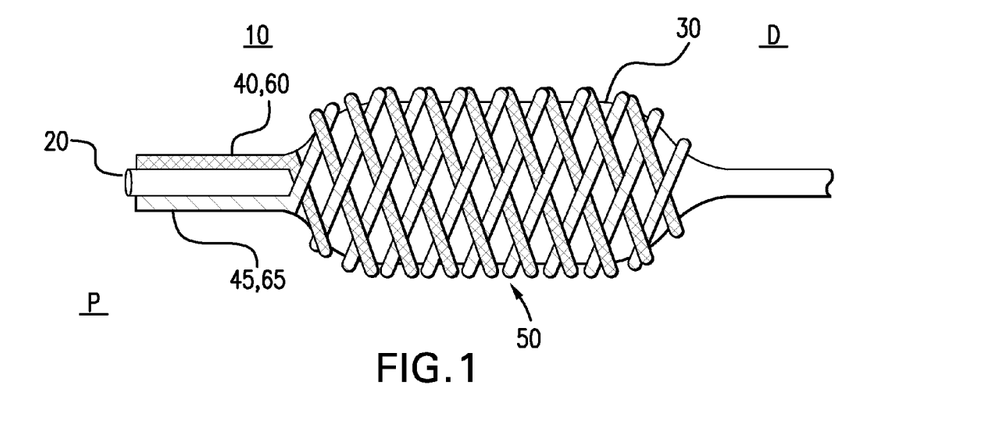
FIG. 1 is a perspective view of a therapeutic agent delivery device according to a first embodiment.
Figure 2:
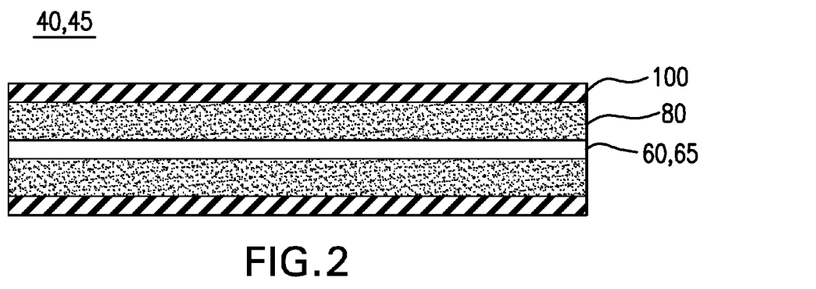
FIG. 2 is a cross-sectional view of a composite cable used in the embodiment illustrated in FIG. 1.

As illustrated in FIGS. 1 and 2, a therapeutic agent delivery device 10 according to a first embodiment includes a first conductive element 60 which is part of a first composite cable 40 and a second conductive element 65 which is part of a second composite cable 45 located on an expandable member 30. The expandable member 30 may be mounted on the distal end of a catheter 20 for delivery to the desired target location, for example, for delivery into the vasculature of the human body. The first composite cable 40 and conductive element 60, and the second composite cable 45 and conductive element 65, may be located on the expandable member 30 in any suitable configuration. In certain embodiments, the composite cable 40 and the composite cable 45 are wound around an outermost surface of the expandable member 30 leading from a proximal end to the distal end of the expandable member in generally opposite helical directions to form a braided arrangement 50, as illustrated in FIG. 1.

Expandable member 30 may be any suitable device capable of being expanded in a radial direction. In its unexpanded position (not shown), the diameter of the expandable member 30 should be such that the catheter 20 and the expandable member 30 move easily throughout the delivery passage, e.g., the vascular system, without causing damage to the tissue. In its expanded position, as illustrated in FIG. 1, the expandable member expands radially to approach the inner surface of the lumen or vessel, i.e., the vessel wall, such that the composite cables 40, 45 are in contact with the lumen or tissue or blood adjacent to and inside the lumen.

In embodiments such as that shown in FIG. 1, the expandable member 30 may be a balloon. Any suitable material may be used for the balloon 30, such as, for example, a polymeric material. Angioplasty balloon materials have been the subject of a number of patents and patent applications, including U.S. Patent Application Publication No. 2007/0208365 to Lee et al. and U.S. Patent Application Publication No. 2007/0208405 to Goodin et al. The disclosures of these applications are expressly incorporated herein by reference. The balloon 30 may be formed, for example, from a high durometer PEBAX®, such as PEBAX® 7233, 7033 or 6333, or NYLON 12®.

Examples of other polymeric materials from which the balloon 30, or layers of the balloon 30, may be formed include polyethylene, HYTREL®, polyester, polyurethane, ABS (acrylonitrile-butadiene-styrene) block copolymer, ABS/Nylon blends, ABS/polycarbonate blends and combinations thereof, styrene-acrylonitrile block copolymers, other acrylonitrile copolymers, polyacrylamide, polyacrylates, polyacrylsulfones polyester/polycaprolactone blends, polyetheretherketone (PEEK), polyethersulfone (PES), polyetherimide (PEI), polyetherketone (PEK), polymethylpentene, polyphenylene ether, polyphenylene sulfide, polyolefins such as polyethylene and polypropylene, olefin copolymers, such as ethylene-propylene copolymer, ethylene-vinyl acetate copolymers, ethylene-vinyl alcohol copolymers and polyolefin ionomers, polyvinyl chloride, polycaprolactam, N-vinyl-pyrrolidone, polyurethanes and polysiloxanes.

The conductive elements 60, 65 may be comprised of any suitable conductive material such as, as just one of many possible examples, a cobalt-based alloy. Conductive materials have been the subject of a number of patents including commonly assigned U.S. Pat. No. 6,592,617 to Thompson. The disclosure of this patent is expressly incorporated herein by reference. In embodiments, the conductive elements 60, 65 may be formed from 316 L stainless steel or a MP35N alloy. Examples of other materials that conductive elements 60, 65 may be formed from are sold under the brand names Elgiloy® and Phynox®. Other metallic materials that may be used include Nitinol nickel-titanium. The conductive elements 60, 65 may also be a wire or strand, such as a polyolefin fiber, coated with conductive material, such as a conductive polymer like polypyrrole. Examples of other suitable conductive polymers are described in commonly assigned U.S. Patent Application Publication No. 2007/0250036 to Volk et al., the disclosure of which is expressly incorporated herein by reference.

As illustrated in FIG. 2, the first composite cable 40 and the second composite cable 45 of the therapeutic agent delivery device 10 according to the first embodiment may also comprise an electrochemical composition 80 and a permeable membrane 100. In this embodiment, the electrochemical composition is located between each conductive element 60, 65 and the respective permeable membrane 100. In this way, the electrochemical composition 80 is inside the composite cable 40, 45. In this manner, the permeable membrane 100 covers the electrochemical composition 80 around each conductive element 60, 65. It will be appreciated that once the therapeutic agent delivery device is assembled as shown in FIG. 1, there are areas in which the first and second conductive elements 60, 65 are separated, and the electrochemical composition 80 is located between the first conductive element 60 and the second conductive element 65.

The electrochemical composition 80 includes a therapeutic agent. Various therapeutic agents are contemplated and are within the spirit and scope of the invention. The therapeutic agent will be dependent upon the condition treated. For example, for the treatment of restenosis, paclitaxel may be used as the therapeutic agent. A number of suitable therapeutic agents that may be used with the invention are known in the art. For example, therapeutic agents that may be used with the invention are disclosed in U.S. Patent Application Publication No. 2008/0107794 to O'Connor et al., the disclosure of which is expressly incorporated herein by reference.

The electrochemical composition 80 includes an electrolyte. Any suitable electrolyte may be used as long as the electrolyte maintains the integrity of the therapeutic agent and is suitable for the electrochemical process in accordance with the invention. In some embodiments, the electrolyte may be any suitable ionized salt such as, for example, phosphate, bicarbonate, calcium, chloride, magnesium, potassium, and/or sodium. Other electrolytes may be used within the scope of the invention.

The electrochemical composition 80 may be formulated with an organic solvent. Any suitable organic solvent is contemplated. Preferably, the organic solvent is biocompatible and non-toxic. For example, in certain embodiments, the solvent may be an organic solvent selected from the group consisting of ethyl acetate and ethanol. A number of suitable solvents that may be used with the invention are known in the art. For example, solvents that may be used with the invention are disclosed in U.S. Pat. No. 7,070,582 to Freyman et al., the disclosure of which is expressly incorporated herein by reference.

The permeable membrane 100 may be comprised of any material suitable for permitting the therapeutic agent to pass across the membrane 100 to the target location 130. In certain embodiments, permeable membrane 100 is formed from a permeable polymer such as, for example, low durometer PEBAX®, such as PEBAX® 2533 or 3533, or polyurethane. Low durometer PEBAX® has been shown to have good permeability and selectivity for ethyl acetate and paclitaxel as discussed in Rezac et al., "Effect of Copolymer Composition on the Solubility and Transport of Water and Methanol in a Series of Polyether Amides," *Journal of Applied Polymer Science*, Vol. 65 (10), pp. 1983-1993 (1997).

The permeable polymer for the permeable membrane 100 may be converted into an ionically conductive polymer electrolyte by the addition of salts such as, for example, $MgCl_2$ or similar salt compounds. Ionically conductive polymers are described in Morisato et al., "Transport properties of PA12-PTMO/$AgBF_4$ solid polymer electrolyte membranes for olefin/paraffin separation," *Desalination*, 145, pp. 347-351 (Sep. 10, 2002); Furtado, et al., "Electrochemical behavior of polyurethane ether electrolytes/carbon black composites and application to double layer capacitor," *Electrochimica Acta*, 46, pp. 1629-1634 (Mar. 15, 2001); and Kujawski et al., "Sweeping gas pervaporation with hollow-fiber ion-exchange membranes," *Desalination*, 162, pp. 129-135 (Mar. 10, 2004).

The therapeutic agent delivery device of FIGS. 1-5 includes and/or is adapted to be connected to a voltage source such that the first and second conductive elements 60, 65 may be connected to the voltage source. A voltage source 70 is shown schematically in FIG. 5. The voltage source may be, for example, a low voltage battery which will generate DC current through the first and second conductive elements 60, 65.

Figure 3:
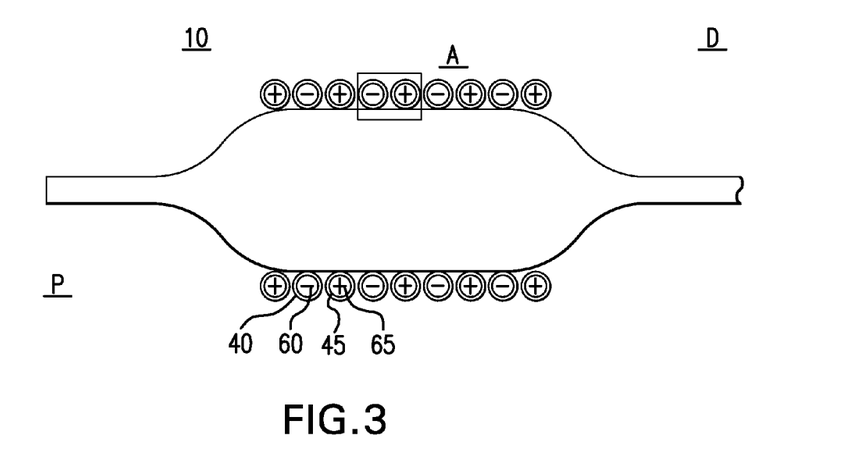
FIG. 3 is a cross-sectional view of the therapeutic agent delivery device illustrated in FIG. 1.

When the first and second conductive elements 60, 65 are connected to the voltage source, a potential is applied such that, as illustrated in FIG. 3, the first conductive element 60 and the second conductive element 65 have different polarities. For example, the first conductive element 60 may have a negative polarity and the second conductive element 65 may have a positive polarity consistent with the structural model of a traditional electrochemical circuit. For purposes of this example, FIG. 3 depicts the first conductive element 60 as the cathode and the second conductive element 65 as the anode. In keeping with this model, the first conductive element 60 having the first polarity is either a cathode or an anode and the second conductive element 65 having the second polarity is the other of either the cathode or the anode. As illustrated in FIG. 3, in braided embodiments such as that illustrated in FIG. 1, the first composite cable 40 and the second composite cable 45 are located in alternating order along a longitudinal plane in the axial direction consistent with the helical structure of the braided arrangement 50.

Figure 4:
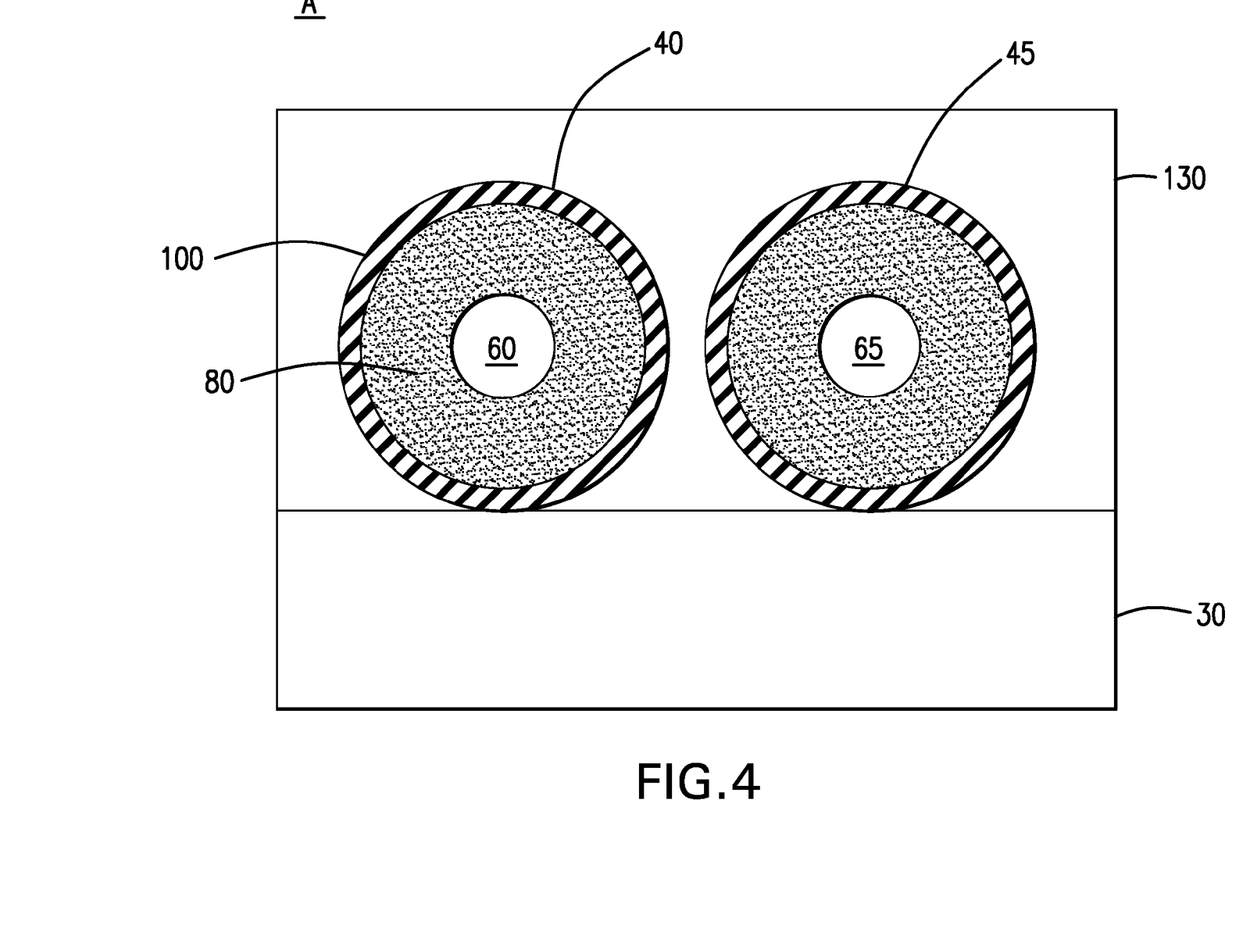
FIG. 4 is an enlarged schematic view of the box "A" in FIG. 3.

FIG. 4 illustrates a magnified section "A" of FIG. 3. In FIG. 4, cross-sectional schematic illustrations of adjacent first composite cable 40 and second composite cable 45 are depicted. FIG. 4 further illustrates the target location or medium 130 at which the therapeutic agent delivery device 10 is placed. The tissue and/or fluid (e.g., blood) at the target location completes an electrical circuit, as described in more detail below. As shown in FIG. 4, when the expandable member 30 is in the expanded position, the composite cables 40, 45 are embedded in medium 130. It is not necessary, however, that the composite cables 40, 45 be fully immersed or embedded in tissue in which the outer surface of the expandable member 30 is implanted. For example, one of ordinary skill in the art will recognize that varying degrees of partial contact with the human tissue or blood are sufficient to complete the electrical circuit.

The target location 130 in this embodiment may be, for example, blood, an inner wall of a blood vessel, human tissue, or any combination thereof. The vessel may be any vessel located within or outside of the body of a patient and suitable for use with the invention. It may include blood-carrying vessels such as the veins, arteries, and chambers of the heart; it may also include the esophagus, the ureters, the intestines, the pockets of fluid located within the individual vertebrae of the spinal column, and any other suitable vessel as apparent to one of skill in the art. Organs and tissues that may be treated by the present invention include any mammalian tissue or organ, whether located in vivo or ex vivo. Non-limiting examples include the vasculature of the heart, the lungs, the brain, the livers, the kidneys, the bladder, the intestines, the stomach, and the pancreas.

Figure 5:
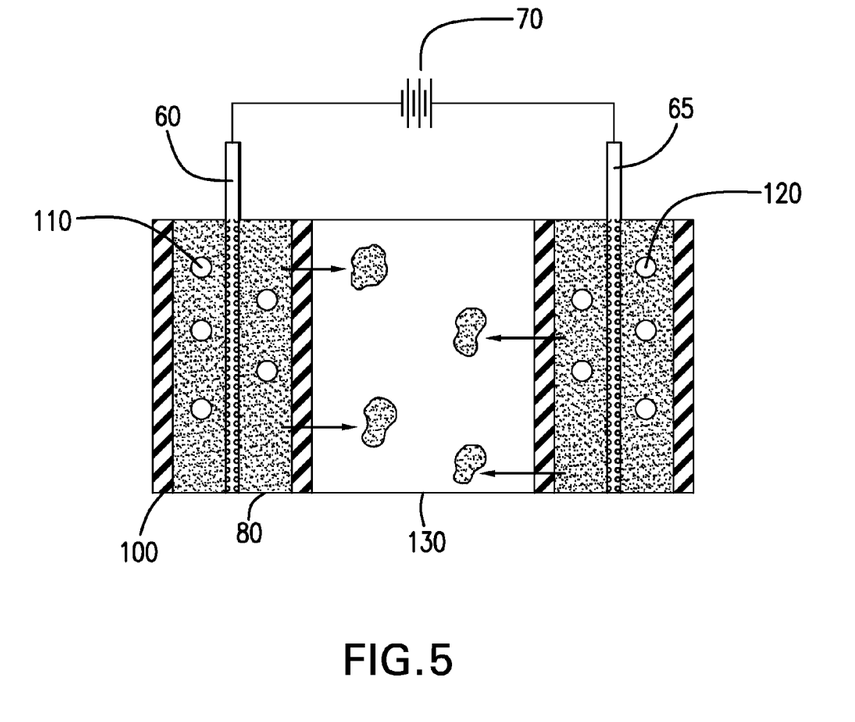
FIG. 5 is a schematic view of the therapeutic agent delivery device according to the first embodiment showing a completed electrochemical circuit.

FIG. 5 shows a schematic diagram of the electrical circuit completed by the tissue and/or fluid at the target location when the therapeutic agent delivery device is deployed and the first and second conductive elements 60, 65 are connected to the voltage source 70. For the purpose of this example, FIG. 5 depicts the first conductive element 60 as the cathode and the second conductive element 65 as the anode. In this example embodiment, the blood and/or tissue 130 acts as an electrolyte, via the natural salts contained therein, that completes the circuit between the anode and cathode akin to the role of a salt bridge in a traditional electrochemical circuit.

When the therapeutic agent delivery device is deployed and the first and second conductive elements 60, 65 are connected to the voltage source 70, an electrochemical reaction occurs at the interface of the first conductive element 60 and the respective electrochemical composition 80 and at the interface of the second conductive element 65 and the respective electrochemical composition 80, as illustrated in FIG. 5. The electrochemical reactions cause the production of $H_2$ gas 110 at the cathode and $O_2$ gas 120 at the anode, resulting in a build-up of pressure within the permeable membranes 100 of the first and second composite cables 40, 45. The build-up of pressure forces the movement of the therapeutic agent through the permeable membrane 100 to the target location 130. For example, when a low durometer PEBAX® is used for the permeable membrane 100, paclitaxel is used for the therapeutic agent and ethyl acetate is used as an organic solvent for the paclitaxel, the build-up of pressure within the first and second composite cables 40, 45 due to the electrochemical production of gas forces the paclitaxel carried by the ethyl acetate to pass through the permeable membrane 100 and thereby elute to the target location 130.

The electrochemical reaction may be any reaction, for example of the type known as oxidation-reduction reactions (hereinafter "redox reaction"), suitable for application in the human body. Redox reactions involve the transfer of electrons and are well known in the art. In certain embodiments such as that illustrated in FIGS. 1-5, the redox reaction may be electrolysis of water. For example, thermodynamics requires 1.23 V for a water electrolysis reaction, such that the overall reaction is indicated in Formula I:

$$2H_2O(l) \rightarrow 2H_2(g) + O_2(g) \quad Eo/V = 1.23 \tag{I}$$

For the individual anodic and cathodic reactions, this translates into the half reactions as indicated in Formula II (cathodic) and Formula III (anodic):

$$2H_2O + 2e^- \rightarrow 2OH^- + H_2 \quad Eo/V = -0.83 \tag{II}$$

$$4OH^- \rightarrow O_2 + 2H_2O + 4e^- \quad Eo/V = +0.4 \tag{III}$$

Formula II represents the cathode half reaction and Formula III represents the anode half reaction. The anodic reaction for neutral electrolyte uses hydroxide ions produced at the cathode. With this electrolysis, applying a voltage from source 70 results in both the oxidation and reduction of the water molecules. In these reactions, water is reduced and split to produce $H_2$ gas 110 and $O_2$ gas 120 at the cathode and anode, respectively. As a result of these half reactions, gas is released causing a pressure build-up that causes the therapeutic agent to pass through the permeable membrane 100. As illustrated in FIG. 5, the reaction represented by Formula I produces $H_2$ gas 110. The conductive element where this reaction occurs is the cathode. The reaction represented by Formula II produces $O_2$ gas 120. The conductive element where this reaction occurs is the anode. One of ordinary skill in the art will recognize that suitable variations to the reactions described above are possible and within the scope and spirit of this invention.

Figure 6:
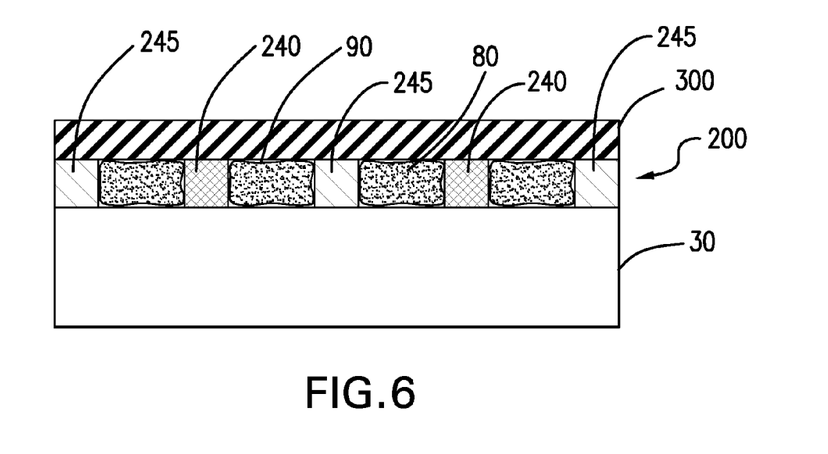
FIG. 6 is a cross-sectional view of a therapeutic agent delivery device according to a second embodiment.

FIG. 6 illustrates a second embodiment. In this embodiment, the therapeutic agent delivery device comprises a first conductive element 240 and a second conductive element 245 located on an expandable member 30. The conductive elements 240, 245 may be, for example, polyolefin fiber coated with polypyrrole or any other suitable conductive material as described above with reference to FIGS. 1-5. In this example, the first and second conductive elements 240, 245 cross each other to form a braided arrangement 200 defining areas or reservoirs 90 bounded by the first conductive element 240 and the second conductive element 245. The electrochemical composition 80 is located in the areas 90 bounded by the first conductive element 240 and the second conductive element 245, and the permeable membrane 300 covers the areas bounded by the first conductive element 240 and the second conductive element 245 in which the electrochemical composition 80 is located. The materials for the various components in this embodiment may be similar to those described above with respect to the first embodiment of FIGS. 1-5.

The operation of the first embodiment of FIGS. 1-5 will now be described with respect to a method of using the therapeutic agent delivery device 10. For explanatory purposes only, this embodiment will be described with reference to restenosis of a coronary artery. One of ordinary skill in the art will readily recognize that the therapeutic agent delivery device 10 may be used in other suitable applications.

In practice, for example, a physician inserts the distal end of the catheter 20 (which is the portion with the therapeutic agent delivery area on the expandable member 30) through, for example, the femoral artery of the patient and guides the therapeutic agent delivery device 10 through the vasculature to the target location 130 in a coronary artery. Once the therapeutic agent delivery area is at the target location, the first conductive element 60 and the second conductive element 65 of the braided arrangement 50 will be connected to the voltage source 70. The voltage source 70 applies a potential to the first and second conductive elements 60, 65. Consequently, as discussed above, the conductive elements 60, 65 behave as an anode or cathode. The space enclosed by the membrane 100, including the electrochemical composition 80 and the respective conductive elements 60, 65, acts as an electrochemical cell. The electrochemical composition 80, for example, a paclitaxel-ethyl acetate-water-phosphate salt formulation, serves as a non-aqueous electrolyte with water content, for example as described in Timbola et al., "Electrochemical Oxidation of Quercetin in Hydro-Alcoholic Solution," *J. Braz. Chem. Soc.*, 17(1), pp. 139-148 (Janaury/February 2006). The blood/tissue at target location 130 completes the electrical circuit by acting as an electrolyte.

In particular, when the voltage source 70 is applied to the first conductive element 60 and the second conductive element 65, the electrochemical reaction causes the release of gas. The release of gas increases pressure in the first and second composite cables 40, 45 which forces the therapeutic agent in the first and second composite cables 40, 45 to pass through the respective permeable membranes 100 to elute to a target location 130. In addition to the build-up of pressure as a result of the electrochemical redox reaction, movement of the electrochemical composition 80 through the membrane 100 may be further facilitated by the electrolytic nature of the membrane 100 itself.

In accordance with certain embodiments of the invention, during the angioplasty procedure, the physician has the ability to turn the power coming from the voltage source 70 on and off as required. The pressure gradient generated within the composite cables 40, 45 allows for fast controlled, "on-demand," transport of the paclitaxel-ethyl acetate formulation across the permeable membrane 100.

The operation of the second embodiment of FIG. 6 is similar to the operation of the first embodiment. Voltage source 70 applies a potential to conductive elements 240 and 245, causing an electrochemical reaction that increases the pressure in the reservoirs 90. The pressure causes the therapeutic agent to pass through permeable membrane 300 to target location 130.

In the embodiments illustrated in FIGS. 1-6, the electrochemical circuit of the devices and methods described herein provides for acute, controlled delivery of therapeutic agent to a diseased site. In this regard, these embodiments provide for a minimally invasive insertion procedure in which the expandable member 30 is in an unexpanded position to avoid disruption of or damage to the tissue in route to the target location. Once at the target location, the expandable member 30 is expanded. Up until this point, the therapeutic agent is maintained within the permeable membrane 100. Unlike conventional methods and devices, the therapeutic agent remains protected from foreign particles in the blood stream or tissue that may dissolve or react with the therapeutic agent until the physician has positioned the therapeutic agent delivery device 10 at the desired location. At this point, the physician is then able to control the amount and rate of application of the therapeutic agent via the electrochemical composition 80 to the target location 130 by manipulating the voltage source 70 driving the electrochemical reactions. In part because the tissue of the target location 130 is part of the electrochemical circuit, improved application and minimized loss of the therapeutic agent to that location can be obtained, producing significantly lower overall costs and improved performance of the device over conventional devices and methods.

Disclosed embodiments have been described with reference to several exemplary embodiments. There are many modifications of the disclosed embodiments which will be apparent to those of skill in the art. It is understood that these modifications are within the teaching of the present invention which is to be limited only by the claims.

What is claimed is:

1. A therapeutic agent delivery device for insertion into a patient's blood vessel, the device comprising:
    a catheter;
    an expandable member mounted on the end of the catheter;
    a first conductive element located on the expandable member and having a first polarity
    a second conductive element located on the expandable member and having a second polarity;
    an electrochemical composition including an electrolyte and a therapeutic agent located between the first conductive element and the second conductive element; and
    a permeable membrane covering the electrochemical composition;
    wherein the first conductive element and the second conductive element are adapted to be connected to a voltage source; and
    wherein when the first conductive element and the second conductive element are connected to the voltage source, an electrochemical reaction occurs causing the therapeutic agent to pass through the permeable membrane and thereby to elute to a target location.

2. The therapeutic agent delivery device according to claim 1, wherein the first conductive element is part of a first composite cable;
    wherein the first composite cable comprises the first conductive element, the electrochemical composition, and the permeable membrane, wherein the permeable membrane surrounds the first conductive element, and wherein the electrochemical composition is located between the first conductive element and the permeable membrane; and
    wherein when the first conductive element and the second conductive element are connected to the voltage source, the electrochemical reaction causes the therapeutic agent in the first composite cable to pass through the permeable membrane of the first composite cable to elute to a target location.

3. The therapeutic agent delivery device according to claim 2, wherein the second conductive element is part of a second composite cable;
    wherein the second composite cable comprises the second conductive element, a second electrochemical composition including an electrolyte and a therapeutic agent, and a second permeable membrane, wherein the second permeable membrane surrounds the second conductive element, and wherein the second electrochemical composition is located between the second conductive element and the second permeable membrane; and
    wherein when the first conductive element and the second conductive element are connected to the voltage source, an electrochemical reaction causes the therapeutic agent in the second composite cable to pass through the second permeable membrane of the second composite cable to elute to a target location.

4. The therapeutic agent delivery device according to claim 1, wherein the electrochemical reaction is the electrolysis of water.

5. The therapeutic agent delivery device according to claim 1, wherein the electrochemical reaction causes a gas to release, the gas causing a pressure that causes the therapeutic agent to pass through the permeable membrane.

6. The therapeutic agent delivery device according to claim 1, wherein the expandable member is a balloon.

7. The therapeutic agent delivery device according to claim 1, wherein the first conductive element and the second conductive element are wound in opposite generally helical directions to form a braided arrangement.

8. The therapeutic agent delivery device according to claim 1, wherein the first conductive element having the first polarity is either a cathode or an anode and the second conductive element having the second polarity is the other of either the cathode or the anode.

9. The therapeutic agent delivery device according to claim 8, wherein when the first conductive element and the second conductive element are connected to the voltage source, the target location at which the therapeutic agent delivery device is placed completes an electrical circuit between the anode and the cathode.

10. The therapeutic agent delivery device according to claim 9, wherein the target location is at least one of blood, an inner wall of a blood vessel and human tissue.

11. The therapeutic agent delivery device according to claim 8, wherein the electrochemical reaction is the electrolysis of water and an electrochemical reaction at the cathode releases hydrogen and an electrochemical reaction at the anode releases oxygen.

12. The therapeutic agent delivery device according to claim 1, wherein the permeable membrane comprises polyether-polyamide block copolymer.

13. The therapeutic agent delivery device according to claim 1, wherein the permeable membrane comprises an ionically conductive polymer.

14. The therapeutic agent delivery device according to claim 1, wherein the therapeutic agent comprises paclitaxel.

15. The therapeutic agent delivery device according to claim 1, wherein the electrolyte comprises a salt.

16. The therapeutic agent delivery device according to claim 1, wherein the electrochemical composition further includes an organic solvent selected from the group consisting of ethyl acetate and ethanol.

17. The therapeutic agent delivery device according to claim 1, wherein the first conductive element and the second conductive element are located on an expandable member and cross each other to form areas bounded by the first conductive element and the second conductive element;
  wherein the electrochemical composition is located in areas bounded by the first conductive element and the second conductive element; and
  wherein the permeable membrane covers the areas bounded by the first conductive element and the second conductive element in which the electrochemical composition is located.

18. A method of delivering a therapeutic agent to a target location in a patient's blood vessel, the method comprising:
  (a) using a therapeutic agent delivery device comprising:
    (i) a catheter;
    (ii) an expandable member mounted on the end of the catheter;
    (iii) a first conductive element located on the expandable member and adapted to be connected to a voltage source;
    (iv) a second conductive element located on the expandable member and adapted to be connected to the voltage source;
    (v) an electrochemical composition located between the first conductive element and the second conductive element at a therapeutic agent delivery area of the device, the electrochemical composition including an electrolyte and a therapeutic agent; and
    (vi) a permeable membrane covering the electrochemical composition;
  (b) positioning the therapeutic agent delivery area of the device at a target location; and
  (c) connecting to the voltage source such that the first conductive element has a first polarity and the second conductive element has a second polarity, thereby causing an electrochemical reaction that causes the therapeutic agent to pass through the permeable membrane and thereby to elute to the target location.

* * * * *